(12) United States Patent
Watkins et al.

(10) Patent No.: US 8,794,821 B2
(45) Date of Patent: Aug. 5, 2014

(54) TORSIONALLY FLEXIBLE, SEALED DRIVE

(75) Inventors: Jeff Watkins, Watchung, NJ (US); Simin Yao, Bridgewater, NJ (US)

(73) Assignee: Eppendorf, Inc., Enfield, CT (US)

( * ) Notice: Subject to any disclaimer, the term of this patent is extended or adjusted under 35 U.S.C. 154(b) by 1188 days.

(21) Appl. No.: 12/528,414

(22) PCT Filed: Feb. 22, 2008

(86) PCT No.: PCT/US2008/054653
§ 371 (c)(1),
(2), (4) Date: Feb. 4, 2010

(87) PCT Pub. No.: WO2008/144089
PCT Pub. Date: Nov. 27, 2008

(65) Prior Publication Data
US 2010/0149907 A1 Jun. 17, 2010

Related U.S. Application Data

(60) Provisional application No. 60/891,048, filed on Feb. 22, 2007.

(51) Int. Cl.
*B01F 7/16* (2006.01)
(52) U.S. Cl.
USPC .......................................................... 366/276
(58) Field of Classification Search
USPC .......................................... 366/276, 278, 243
See application file for complete search history.

(56) References Cited

U.S. PATENT DOCUMENTS

| | | | | |
|---|---|---|---|---|
| 2,702,693 A | * | 2/1955 | Kay | 366/243 |
| 2,775,434 A | * | 12/1956 | Clemens | 366/120 |
| 2,877,994 A | | 3/1959 | Jones | |
| 3,182,970 A | | 5/1965 | Ivanoff | |
| 3,311,354 A | * | 3/1967 | Wilson | 366/248 |
| 3,384,354 A | * | 5/1968 | Albrecht et al. | 366/118 |
| 3,572,651 A | * | 3/1971 | Harker | 366/185 |

(Continued)

FOREIGN PATENT DOCUMENTS

WO 01/28608 A2 4/2001

OTHER PUBLICATIONS

International Search Report and Written Opinion issued for PCT/US08/54653, dated Jun. 24, 2008.

(Continued)

*Primary Examiner* — Tony G Soohoo
(74) *Attorney, Agent, or Firm* — Fox Rothschild LLP; Richard C. Woodbridge; Ryan N. Miller

(57) ABSTRACT

A simple, robust and low-cost torsionally flexible, sealed drive that allows external drives to provide agitation within a container. A torsionally flexible tube is sealed to a torsionally rigid portion of a container. A second end of the tube is sealed to a driven element within the container. The driven element is coupled to a drive-shaft that is partly contained within the tube. Motion of the protruding end of the drive shaft imparts a corresponding motion to the driven element, while maintaining a water-tight seal between container and drive-shaft. One useful motion is a rotary oscillation. A stepper motor may operate via such a drive to impart a rotary oscillation to an impellor in a bioreactor, or mixing container, suitable for agitating a cell culture in a nutrient medium or hydrating a powdered media in water. The drive is suited to use in disposable bioreactors and mixers.

21 Claims, 4 Drawing Sheets

(56) References Cited

U.S. PATENT DOCUMENTS

| | | | |
|---|---|---|---|
| 4,112,518 A * | 9/1978 | Garlinghouse | 366/219 |
| 4,979,829 A * | 12/1990 | Allen | 366/66 |
| 3,252,689 A | 5/1996 | Blomgren, Sr. et al. | |
| 6,491,422 B1 | 12/2002 | Rutten et al. | |
| 6,883,960 B2 * | 4/2005 | Reeder et al. | 366/243 |
| 7,249,880 B2 * | 7/2007 | Zambaux | 366/277 |
| 7,431,494 B2 * | 10/2008 | Zambaux | 366/144 |
| 2002/0172092 A1 * | 11/2002 | Reeder et al. | 366/270 |
| 2005/0078552 A1 * | 4/2005 | Zambaux | 366/241 |
| 2005/0239199 A1 | 10/2005 | Kunas et al. | |

OTHER PUBLICATIONS

Extended European Search Report issued Oct. 16, 2013 for European Appln. No. 08795797.3 (6 pages).

* cited by examiner

TORSIONALLY FLEXIBLE, SEALED DRIVE

CROSS REFERENCE TO RELATED APPLICATION

The present application is a 35 U.S.C. §371 National Phase application of International Application Serial No. PCT/US2008/54653 filed Feb. 22, 2008, which is related to, and claims priority from, U.S. Provisional Patent Application No. 60/891,048 filed on Feb. 22, 2007 by Watkins et al. titled "Mixing Mechanism for Disposable Mixer or Bioreactor", the contents of which are hereby incorporated by reference.

TECHNICAL FIELD

The present invention is related to methods and apparatus for transferring oscillatory rotary motion across a sterile seal, and more particularly to transferring such motion from a motor outside a container to a mixing impellor within the container.

BACKGROUND ART

Disposable, one-time use pipettes and micro-containers have been standard in the bio-molecular community for some time. They provide an easy and efficient way to obtain sterile conditions and eliminate cross-contamination between cultures and nutrient medium. More recently, the pharmaceutical and biotechnology industries have begun to apply the same principle to larger equipment, and begun making and using disposable, one-use sterile bioreactors, mixers and containers of up to 1000 liters capacity.

A bioreactor, or mixer, is a container with multiple ports for adding and removing ingredients and with a mechanism for agitating the ingredients within the container. The containers are typically available in three forms often referred to as hard shell, soft shell and a combination of hard and soft shell. A hard shell container holds its shape without support or internal pressure and is typically made of material such as, but not limited to, stainless steel or rigid plastics such as polycarbonate or ABS rubber. A soft shell container is typically made of flexible plastic films such as, but not limited to, polyethylene, polyurethane, santoprene or flexible vinyl, or combinations thereof. If a soft shell container is required to conform to a specific geometry, it may be pressurized and may additionally have a rigid supporting frame, or container, to ensure confirmation to the required geometry. The combination soft shell, hard shell containers are typically used to form a container that varies in shape or volume during a use cycle.

The entire bioreactor, including the container, ports and mixing mechanism, are typically sterilized prior to use by well-known sterilization technology such as, but not limited to, high temperature steam or gamma ray radiation. To keep the bioreactor, or mixer, sterile during the life cycle of its use, all penetrations of the containers must be sealed. Providing an adequate seal for agitation mechanisms is problematic as the agitation mechanisms typically have a driving motor external to the container and an impellor, or other agitating mechanism, internal to the container. In order to impart motion to the agitating mechanism, typically rotary motion to an impellor, the drive shaft must move relative to the opening in the container. The challenge is how to form an effective seal between the moving drive shaft and the container. The seal must be water-tight and allow many weeks of continuous operation without using lubricants that may contaminate the contents of the container.

In one-use mixers, or bioreactors, the challenge is made more difficult because low cost is a further, important requirement of disposable equipment. Most seals that allow rotary motion are complex and, therefore, expensive. What is needed is a simple, robust, low-cost, sealed drive that allows an external drive mechanism to provide internal agitation to the contents of a container.

DISCLOSURE OF INVENTION

The present invention relates to a torsionally flexible, sealed drive apparatus that is simple, robust and low-cost. The torsionally flexible, sealed drive is capable of, for instance, allowing an external drive mechanism to provide internal agitation to the contents of a container.

In a preferred embodiment, a torsionally flexible tube has one end sealed to a torsionally rigid barrier element that surrounds an aperture in a container. A second end of the torsionally flexible tube is sealed to a driven element contained in the container. The driven element is in turn coupled to one end of a drive shaft that is partly contained within the torsionally flexible tube. In this way a motion applied to the other end of the drive shaft, that protrudes from the container imparts a corresponding motion to the driven element within the container, while maintaining a water-tight seal between the container and the drive shaft.

One useful motion that may be imparted to the driven element by the torsionally flexible, sealed drive apparatus of this invention is a rotary oscillatory motion comprising a clockwise motion of some number of degrees followed by a corresponding anticlockwise motion. A stepper motor may, for instance, operate via a torsionally flexible, sealed drive apparatus to impart a rotary oscillatory motion to an impellor in a bioreactor, or mixing container. Such a motion, of appropriate amplitude, has been found to be suitable for agitating a cell culture in a nutrient medium or hydrating a powdered media in high purity water. Being simple, and therefore low cost, the torsionally flexible, sealed drive of this invention is particularly suited to single-use, disposable bioreactor and mixers.

In a further preferred embodiment, a torsionally flexible tube has one end sealed to a torsionally rigid barrier element that surrounds an aperture in a container. A second end of the torsionally flexible tube is sealed to the end of a drive shaft that is external to the container. The drive shaft, which is partly contained within the torsionally flexible tube, has its other end coupled to a driven element within the container. In this way a motion applied to the first end of the drive shaft that protrudes from the container, imparts a corresponding motion to the driven element within the container, while maintaining a water-tight seal between the container and the drive shaft.

These and other features of the invention will be more fully understood by references to the following drawings.

BEST MODE FOR CARRYING OUT THE INVENTION

The present invention relates to apparatus and methods for torsionally flexible, sealed drives, and particularly to their use in providing agitation to a contained fluid using a drive motor external to the container.

Such a torsionallly flexible sealed drive is a simple, robust mechanism that allows, for instance, oscillating rotary motion to be imparted from a stepper motor external to a container, to an impellor internal to the container. Such oscillatory rotary motion of the impellor has been found to be effective in bioreactors and mixers. In particular, imparting an oscillating rotary motion of approximately +/−270 degrees to an impellor was found to an effective way to agitate a cell culture in a nutrient medium.

Being simple, and therefore inexpensive, a torsionally flexible, sealed drive is well suited for use in disposable, one-time bioreactors and mixers, where cost is a major factor.

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

Figure 1:
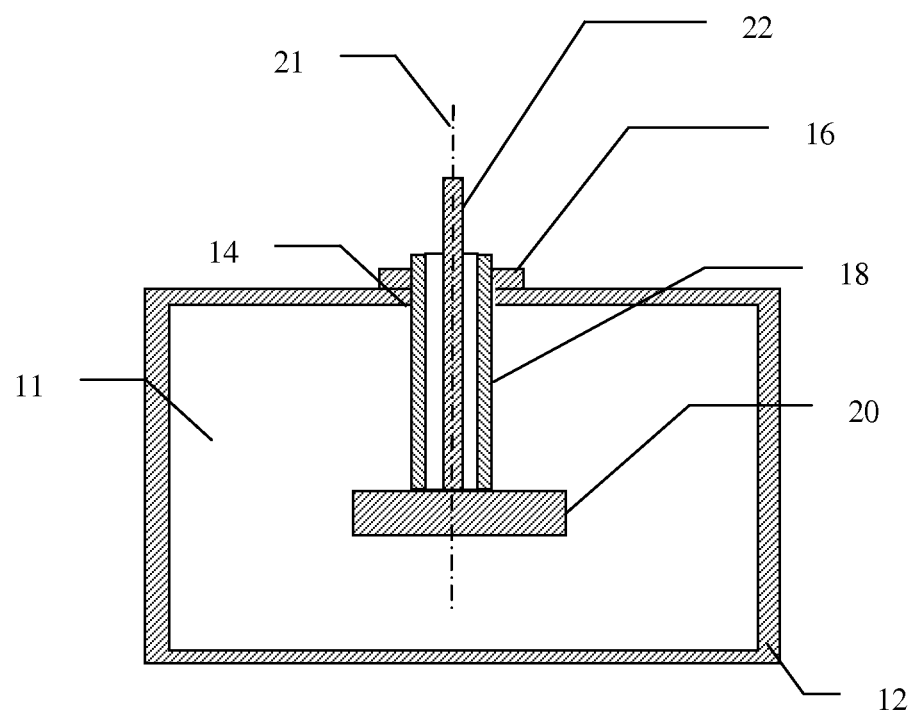
FIG. 1 shows a schematic cross-section of an exemplary embodiment of a torsionally flexible sealed drive in accordance with the present invention.

FIG. 1 shows a schematic cross-section of an exemplary embodiment of a torsionally flexible, sealed drive 10 in accordance with the present invention. The torsionally flexible, sealed drive 10 comprises a container 12 having an aperture 14. Surrounding the aperture 14 is an optional, torsionally rigid flange 16. The optional, torsionally rigid flange 16 provides a torsionally rigid barrier element in the event that the container 12 is torsionally flexible. If the container 12 is torsionally rigid, the container 12 acts as the torsionally rigid barrier element and there may then be no need for the optional, torsionally rigid flange 16.

A torsionally, flexible tube 18 has one end in sealed contact with the optional, torsionally rigid flange 16 and the aperture 14 in the container 12. The other end of the torsionally, flexible tube 18 is in sealed contact with a driven element 20. The driven element 20 is in turn connected to one end of a torsionally, rigid drive shaft 22. The connection between the driven element 20 and the torsionally, rigid drive shaft 22 may, for instance, be a removable connection. The torsionally, rigid drive shaft 22 may be partially located within the torsionally, flexible tube 18 and, in this embodiment, is sealed off from the interior portion 11 of the container 12.

The torsionally flexible, sealed drive 10 is configured such that motion imparted to the end of the rigid drive shaft 22 that protrudes from the torsionally, flexible tube 18 and, therefore, from the interior portion 11 of the container 12, results in a corresponding motion being imparted to the driven element 20. In particular, a rotary motion applied to the external end of the rigid drive shaft 22 results in a corresponding rotary motion being imparted to the driven element 20. The maximum extent of the rotary motion may be determined by the material properties, and the length, of the torsionally, flexible tube 18. One useful motion that may be imparted to the driven element 20 via such a torsionally, flexible, sealed drive 10 is an oscillating rotary motion. Such rotary oscillations may extend for several turns in either direction, or may be of more limited extent in each direction. The motion may also be halted for a brief time at each extreme of the oscillation so as to, for instance, reduce turbulence in a liquid being agitated.

As discussed previously, the container 12 may be one of three forms typically referred to as hard shell, soft shell and a combination of hard and soft shell. Hard shell containers are typically made of material such as, but not limited to, stainless steel or rigid plastics such as polycarbonate or ABS rubber, while a soft shell container is typically made of flexible plastic films such as, but not limited to, polyethylene, polyurethane, santoprene or flexible vinyl, or combinations thereof. The combination soft shell, hard shell containers are typically used to form a container that varies in shape or volume during a use cycle.

The optional torsionally, rigid flange 16 may be in sealed connection with the container 12 and the torsionally, flexible tube 18. The optional, torsionally, rigid flange 16 may, for instance, provide a torsionally, rigid support for a flexible container 12.

The sealed connections between the various elements may, for instance, be formed by any suitable, well-known method including, but not limited to, mechanical fastening including push fitting, solvent bonding, gluing, fusion bonding, hot gas welding, vibration welding, ultrasonic welding, induction welding or dielectric welding.

Figure 2:
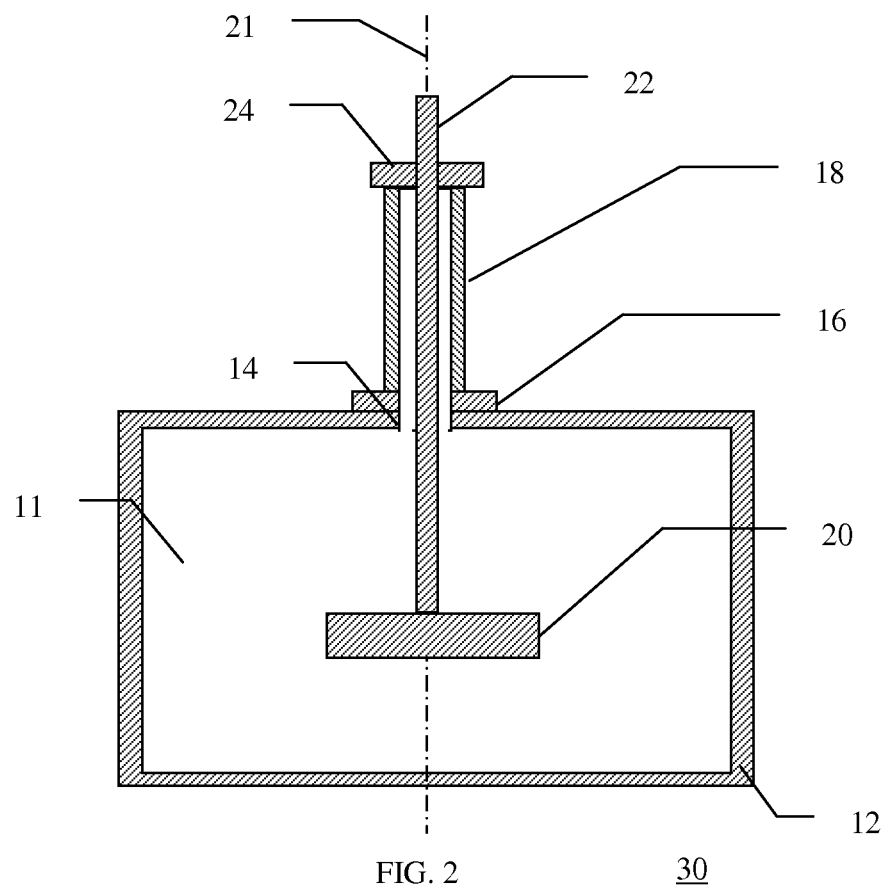
FIG. 2 shows a schematic cross-section of a further, exemplary embodiment of a torsionally flexible sealed drive in accordance with the present invention.

FIG. 2 shows a schematic cross-section of a further, exemplary embodiment of an external torsionally flexible sealed drive 30 in accordance with the present invention. The external torsionally flexible sealed drive 30 comprises a container 12 having an aperture 14. An optional, torsionally, rigid flange 16 may surround the aperture 14 and be in sealed connection with the container 12. The optional, torsionally rigid flange 16 provides a torsionally rigid barrier element in the event that the container 12 is torsionally flexible. If the container 12 is torsionally rigid, the container 12 acts as the torsionally rigid barrier element and there may then be no need for the optional, torsionally rigid flange 16.

A torsionally, flexible tube 18 has a first end in sealed contact with the container 12 and, if necessary, the optional, torsionally, rigid flange 16. The torsionally, flexible tube 18 protrudes outward, exterior to the container 12. The second end of the torsionally, flexible tube 18 may be in sealed connection with a torsionally, rigid drive shaft 22 that is at least partially contained within the torsionally, flexible tube 18. The sealed contact between the torsionally, flexible tube 18 and the torsionally, rigid drive shaft 22 may include a cap element 24 that may be torsionally rigid. The torsionally, rigid drive shaft 22 may, for instance, be in sealed connection with the cap element 24 that is in turn in sealed connection with the torsionally, flexible tube 18. The end of the torsionally, rigid drive shaft 22 that extends into the interior portion 11 of the container 12 may be attached to a driven element 20.

The external torsionally flexible sealed drive 30 is configured such that a motion applied to the end of the torsionally, rigid drive shaft 22 that protrudes out of the torsionally, flexible tube 18 external to the container 12 imparts a corresponding motion to the driven element 20. In particular, a rotary motion applied to the external end of the torsionally, rigid drive shaft 22 imparts a corresponding rotary motion to the driven element 20. As with the torsionally flexible, sealed drive 10, the maximum extent of the rotary motion of the external torsionally flexible sealed drive 30 may be determined by the material properties, and the length, of the flexible tube 18. One useful motion that may, for instance, be imparted to the driven element 20 is an oscillating rotary motion. Such oscillations may, for instance, extend for several turns in either direction, or may be of more limited extent in each direction, or have some range in between. The motion may also be halted for a period of time at each extreme of the oscillation before motion in the opposite direction is begun to, for instance, reduce turbulence in a liquid being agitated.

Figure 3:
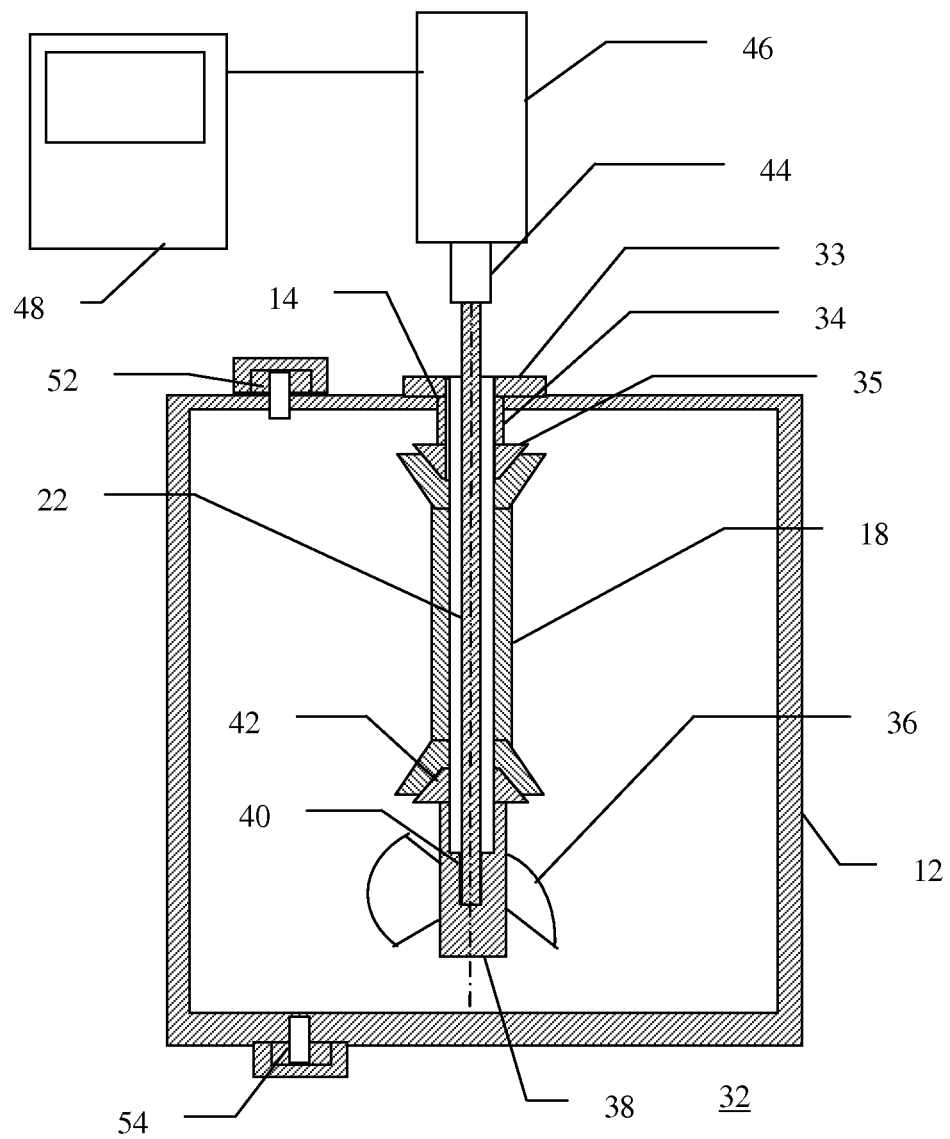
FIG. 3 shows a schematic cross-section of an exemplary embodiment of a bioreactor system in accordance with the present invention.

FIG. 3 shows a schematic cross-section of a mixer or bioreactor system 32 having an internal torsionally flexible, sealed drive 10. Such a system may comprise a container 12 having an aperture 14. A torsionally rigid hose barb 34 may extend through the aperture 14 and be in sealed contact with the container 12, having a barbed end 35 extending into the interior of the container 12. The torsionally rigid hose barb 34 may also have a torsionally rigid flange end 33 that may also be in sealed connection with the container 12. A torsionally, flexible tube 18 has a first end in sealed connection with the barbed end 35 of the torsionally rigid hose barb 34. A second end of the torsionally, flexible tube 18 may be in sealed connection with an impellor 36. The impellor 36 may have a central shaft element 38 that may have a drive coupling recess 40 and a hose barb end 42. The hose barb end 42 of the central shaft element 38 may be sealably connected to the torsionally, flexible tube 18. The drive coupling recess 40 may, for instance, be fluted or keyed, or otherwise shaped to allow releasable connection to a complementary shaped end of the torsionally, rigid drive shaft 22. The torsionally, rigid drive shaft 22 may be located partially within the flexible tube 18 with a drive end extending beyond the torsionally rigid flange end 33 such that a motion imparted to the drive end of the torsionally, rigid drive shaft 22 imparts a corresponding motion to the impellor 36. The drive end of the torsionally, rigid drive shaft 22 may, for instance, be connected by a motor coupling 44 to a suitable drive unit such as a stepper motor 46. The stepper motor 46 may be controlled by suitable motor control electronics 48.

The container 12 typically also has one or more sealable inlet ports 52 and one or more sealable outlet ports 54.

In typical use of the mixer or bioreactor system 32, the ingredients to be agitated enter the container 12 via one or more of the sealable inlet ports 52. Typical ingredients include, but are not limited to, powdered media to be hydrated, high purity water to hydrate the media, and mixtures of cells in nutrient buffer. Once in the container 12, the ingredients are agitated by the motion of the impellor 36. In a preferred embodiment the agitating motion of the impellor 36 is a rotary oscillatory motion. In a preferred embodiment, a clockwise rotary motion of approximately 270 degrees may be alternated with an anticlockwise motion of the same magnitude. At the extremes of the motion the impellor may be held stationary for approximately two seconds, though this could be as little as a tenth of a second to as long as several minutes. A full cycle of the motion may take approximately four seconds, though this may be as little as half a second or as long as thirty seconds.

In alternate embodiments of the invention, the rotary oscillatory motion may be as little as 5 or 10 degrees in clockwise or anti-clockwise extent or it may be limited to some intermediate degree such as, but not limited to, 20, 30, 40, 50, 60, 70, 80, 90, 100, 110, 120, 130, 140, 150, 160, 170, 180, 190, 200, 210, 220, 230, 240, 250 or 260 degrees. In further alternate embodiments of the invention, the rotary oscillatory motion may be as large as 360 degrees, or 720 degrees in clockwise or anti-clockwise extent.

The rotary oscillatory motion of the impellor may be provided by the stepper motor 46 under the control of suitable motor control electronics 48. The stepper motor 46 imparts the required motion to the motor coupling 44 that in turn imparts a corresponding motion to the rigid drive shaft 22 that in turn imparts a corresponding motion to the central shaft element 38 via the drive coupling recess 40. The central shaft element 38 then imparts the required motion to the impellor 36 that then agitates the ingredients contained within the container 12. Once agitation is complete, the ingredients may be removed from the container via one or more of the sealable outlet ports 54.

In a preferred embodiment, the container 12 and all elements that are directly, or indirectly, sealingly attached to the container 12 are disposable elements. The disposable elements are made of materials that may be sterilized for one time use and are sufficiently inexpensive to be disposed of after a single cycle of use. Such materials typically include a range of rigid, semi-rigid and flexible plastics including, but not limited to, silicone, polycarbonate, polypropylene, polysulfone, polyurethane, santoprene, flexible vinyl (FPVC), low density and linear low density polyethylene (LDPE and LLDPE), flexible nylon 11 and nylon 12, and high density polyethylene (HDPE), or some combination thereof.

A suitable motor control electronics 48 may, for instance be a PDO2035 stepper drive as supplied by Applied Motion Products Inc. of Watsonville, Calif. The PDO2035 stepper drive has a digital oscillator mode with precise speed control that may be configured to automatically ramp between speeds and has acceleration and deceleration rates that may be set by an on board potentiometer, and may be adjusted from 10 to 12,000 steps/sec/sec.

The stepper motor 46 may, for instance, be a NEMA 11, 14, 17 or 23 motor as supplied by Applied Motion Products Inc. of Watsonville, Calif. Such motors have electronic gearing and may be configured to have any resolution from 200 to 65,535 steps per revolution.

The impellor 36 may, for instance, be a plastic impellor supplied by Advanced Air International Inc. of Riviera Beach, Fla.

The torsionally rigid hose barb 34 may, for instance, be a hose barb supplied by Inplex LLC of Des Plaines Ill. 60018 and made of a material such as, but not limited to, acetal, chrome-plated brass, polycarbonate, polypropylene, polysulfone or stainless steel.

The torsionally, flexible tube 18 may, for instance, be a portion of torsionally flexible tubing supplied by Inplex LLC of Des Plaines Ill. 60018 and made of a material such as, but not limited to silicone, polyurethane, santoprene, flexible vinyl (FPVC), low density and linear low density polyethylene (LDPE and LLDPE), flexible nylon 11 and nylon 12, or some combination thereof. The torsionally, flexible tube 18 may also, for instance, be a portion torsionally semi-rigid tubing supplied by Inplex LLC of Des Plaines Ill. 60018 and made of a material such as, but not limited to polypropylene (PP) and high density polyethylene (HDPE), or some combination thereof. The torsionally, flexible tube 18 may also be made of some combination of rigid and semi-rigid materials.

Figure 4:
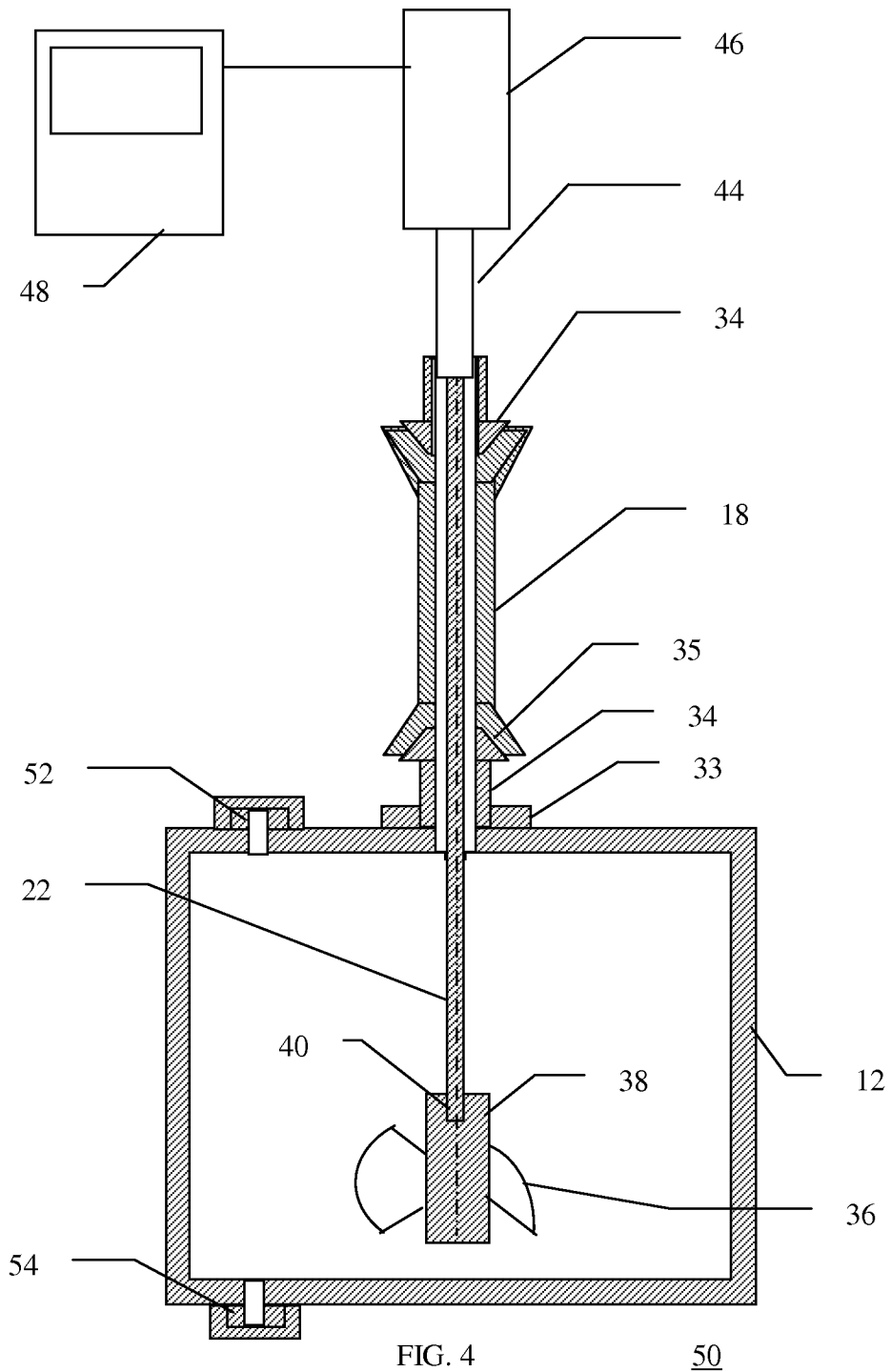
FIG. 4 shows a schematic cross-section of a further, exemplary embodiment of a bioreactor system in accordance with the present invention.

FIG. 4 shows a schematic cross-section of a mixer or bioreactor system 50 having an external torsionally flexible sealed drive 30. Such a system may comprise a container 12 having an aperture 14. A torsionally rigid hose barb 34 may have a torsionally rigid flange end 33 that surrounds the aperture 14 and is sealingly connected to the container 12. The barbed end 35 of the torsionally rigid hose barb 34 is situated so as to protrude outward, external to the container 12. The barbed end 35 of the torsionally rigid hose barb 34 may be sealingly connected to a first end of the torsionally, flexible tube 18. A second end of the torsionally, flexible tube 18 may be sealingly attached to a motor coupling 44 via a torsionally rigid hose barb 34.

The motor coupling 44 may be attached at a first end to a rigid drive shaft 22 that is partially enclosed by the torsionally, flexible tube 18 and may extend into the interior of the container 12. The torsionally rigid drive shaft 22 may be connected to an impellor 36 via a central shaft element 38 that may have a drive coupling recess 40.

The motor coupling 44 may be attached at a second end to a stepper motor 46 that may be connected to, and under the control of, suitable motor control electronics 48.

In a preferred mode of use of the mixer or bioreactor system 50, ingredients to be agitated are loaded into the container 12 via one or more of the sealable inlet ports 52. The stepper motor 46 may then be made to perform a suitable rotary oscillator motion by the motor control electronics 48. The rotary oscillatory motion of the stepper motor 46 induces a corresponding rotary oscillatory motion of the impellor 36, resulting in agitation of the ingredients contained in the container 12. The rotary oscillation of the stepper motor 46 may be transferred to the impellor 36 via the motor coupling 44, the torsionally rigid drive shaft 22 and the central shaft element 38. The maximum possible extent of the rotary oscillatory motion, in either a clockwise or anti-clockwise direction, may be determined by the material properties of the flexible tube 18 and the length of the flexible tube 18. For a typical silicone, or equivalent plastic tube, having an outer diameter of about 0.8 cm and a wall thickness of about 1 mm, and a length of about 12 cm, a range of oscillation of about +/−270 degrees, at a few second cycle, may be sustained for the many weeks of continuous operation for which even a one-time use bioreactor may be required to operate.

Once the ingredients in the container 12 have been agitated for the required amount of time, which may be as long as six weeks, the agitated ingredients may be removed from the container via the sealed outlet port 54.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

INDUSTRIAL APPLICABILITY

In the fields of pharmaceutical and biotechnology manufacturing there is significant interest in simple, robust, low-cost, sealed drive that allows an external drive mechanism to provide internal agitation to a liquid in a container such as the torsionally flexible sealed drive of the present invention. Such a torsionally flexible sealed drive would be of considerable utility as, for instance, in single-use, disposable mixer and bioreactors.

What is claimed:

1. A torsionally flexible, sealed drive apparatus, comprising:
a torsionally flexible tube having a first end in fixed sealed cooperation with an aperture in a substantially torsionally rigid barrier element, and a second end in fixed sealed cooperation with a first end of a drive shaft, and wherein said drive shaft is partially disposed within said torsionally flexible tube and said second end of the flexible tube is rotatable relative to the first end of the flexible tube about a central axis such that said drive shaft is rotationally oscillatable about the central axis.

2. The apparatus of claim 1 further comprising a container and wherein said torsionally rigid barrier element surrounds an aperture in said container.

3. The apparatus of claim 2, wherein said sealed cooperation of said second end of said torsionally flexible tube and said first end of said drive shaft further comprises a driven element contained in said container, and wherein said second end of said torsionally flexible tube is in sealed cooperation within said driven element, and wherein said first end of said drive shaft is adapted to couple with said driven element such that oscillation of said drive shaft about a central axis imparts a corresponding oscillation to said driven element.

4. The apparatus of claim 3 wherein said driven element is driveable in a rotary oscillatory motion comprising a clockwise motion of at least 10 degrees followed by an anticlockwise motion of at least 10 degrees.

5. The apparatus of claim 3 wherein said driven element is driveable in a rotary oscillatory motion comprising a clockwise motion of at least 270 degrees followed by an anticlockwise motion of at least 270 degrees.

6. The apparatus of claim 3 wherein said drive shaft is further adapted to releasably couple with said driven element.

7. The apparatus of claim 3 wherein said driven element is an impellor.

8. The apparatus of claim 3 wherein said container is a collapsible vessel.

9. The apparatus of claim 3 further comprising a stepper motor coupled to a second end of said drive shaft.

10. The apparatus of claim 2, further comprising a driven element contained in said container, and wherein a second end of said drive shaft is adapted to couple with said driven element, such that oscillation of said drive shaft about a central axis imparts a corresponding oscillation to said driven element.

11. The apparatus of claim 10 wherein said driven element is driveable in a rotary oscillatory motion comprising a clockwise motion of at least 10 degrees followed by an anticlockwise motion of at least 10 degrees.

12. The apparatus of claim 10 wherein said driven element is driveable in a rotary oscillatory motion comprising a clockwise motion of at least 270 degrees followed by an anticlockwise motion of at least 270 degrees.

13. The apparatus of claim 10 wherein said driven element is an impellor.

14. The apparatus of claim 10 wherein said container is a collapsible vessel.

15. The apparatus of claim 10 further comprising a stepper motor coupled to a first end of said drive shaft.

16. The apparatus of claim 15 wherein said stepper motor is releasably coupled to said first end of said drive shaft.

17. A method of providing oscillating, rotary motion across a sealed barrier, comprising:
providing a torsionally flexible tube having a first end in fixed sealed cooperation with an aperture in a substantially torsionally rigid barrier element, and a second end in fixed sealed cooperation with a first end of a drive shaft, said second end of the flexible tube being rotatable relative to the first end of the flexible tube about a central axis, and wherein said drive shaft is partially disposed within said torsionally flexible tube; and
imparting an oscillating, rotary motion to said drive shaft about said central axis.

18. The method of claim 17 further comprising providing a container such that said torsionally barrier element surrounds an aperture in said container.

19. The method of claim 17, further comprising providing a driven element contained in said container, in sealed cooperation of said second end of said torsionally flexible tube and adapted to couple with said drive shaft, thereby providing said sealed cooperation between said second end of said torsionally flexible tube and said drive shaft.

20. The method of claim 17 further comprising providing a driven element contained in said container, and adapted to couple with a second end of said drive shaft.

21. A mixer assembly comprising:
a container defining an aperture thereinto; and
a torsionally flexible, sealed drive apparatus including a torsionally flexible tube having a first end in fixed sealed cooperation with the aperture of the container, and a second end in fixed sealed cooperation with a first end of a drive shaft,
wherein said drive shaft is partially disposed within said torsionally flexible tube and said second end of the flexible tube is rotatable relative to the first end of the flexible tube about a central axis such that said drive shaft is rotationally oscillatable about the central axis.

* * * * *